US010915222B2

(12) United States Patent
Ash et al.

(10) Patent No.: US 10,915,222 B2
(45) Date of Patent: Feb. 9, 2021

(54) MULTI-DISCIPLINARY TEAM WORKSPACE

(71) Applicant: CERNER INNOVATION, INC., Kansas City, KS (US)

(72) Inventors: Michael A. Ash, Parkville, MO (US); Heather Owen, Kansas City, MO (US); J D Tyler, Leawood, KS (US); Daniel Stocksick, Liberty, MO (US); Pramod Pagadala, Overland Park, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 0 days.

(21) Appl. No.: 13/964,413

(22) Filed: Aug. 12, 2013

(65) Prior Publication Data

US 2015/0012298 A1 Jan. 8, 2015

Related U.S. Application Data

(60) Provisional application No. 61/842,125, filed on Jul. 2, 2013.

(51) Int. Cl.

| | |
|---|---|
| ***G16H 50/20*** | (2018.01) |
| ***G16H 10/60*** | (2018.01) |
| ***G06F 3/0481*** | (2013.01) |
| ***G06F 19/00*** | (2018.01) |

(52) U.S. Cl.

CPC ...... *G06F 3/04817* (2013.01); *G06F 19/3418* (2013.01); *G16H 50/20* (2018.01)

(58) Field of Classification Search

CPC .... G06Q 50/22; G06Q 50/24; G06F 3/04817; G06F 19/3418; G16H 50/20; G16H 10/60; G16H 15/00

USPC .......................................................... 705/2–3

See application file for complete search history.

(56) References Cited

U.S. PATENT DOCUMENTS

| | | | | |
|---|---|---|---|---|
| 5,823,949 | A * | 10/1998 | Goltra | A61B 5/00 128/924 |
| 5,841,436 | A | 11/1998 | Nakamura et al. | |
| 6,208,974 | B1 | 3/2001 | Campbell et al. | |
| 7,890,341 | B2 * | 2/2011 | McNally | G06F 19/322 705/2 |
| 8,510,126 | B2 * | 8/2013 | Martin et al. | 705/2 |
| 8,775,196 | B2 | 7/2014 | Simpson et al. | |
| 2002/0029157 | A1 * | 3/2002 | Marchosky | G06F 19/3418 705/3 |
| 2006/0195793 | A1 | 8/2006 | Feihl et al. | |
| 2007/0143149 | A1 * | 6/2007 | Buttner | G06F 19/322 705/3 |

(Continued)

OTHER PUBLICATIONS

Non-Final Office Action dated Mar. 24, 2016 in U.S. Appl. No. 13/964,415, 21 pages.

(Continued)

*Primary Examiner* — Eliza A Lam

(74) *Attorney, Agent, or Firm* — Shook, Hardy & Bacon L.L.P.

(57) ABSTRACT

Methods, systems, and computer-storage media are provided for facilitating the care of a patient by a multi-disciplinary care team. A graphical user interface presents one or more clinical problems associated with a patient. For each clinical problem, actionable care team icons are presented that, among other things, identify care teams responsible for caring for the clinical problem and any actions taken by the care teams to address the clinical problem.

15 Claims, 7 Drawing Sheets

(56) References Cited

U.S. PATENT DOCUMENTS

| | | | | |
|---|---|---|---|---|
| 2010/0010833 | A1* | 1/2010 | Langdon | G06F 19/327 705/3 |
| 2012/0011428 | A1 | 1/2012 | Chisholm | |
| 2012/0131507 | A1 | 5/2012 | Sparandara et al. | |

OTHER PUBLICATIONS

Final Office Action dated Apr. 13, 2016 in U.S. Appl. No. 13/964,408, 11 pages.
First Action Interview Office Action dated Oct. 6, 2015 in U.S. Appl. No. 13/964,408, 8 pages.
Final Office Action dated Nov. 20, 2015 in U.S. Appl. No. 13/964,415, 19 pages.
First Action Interview Preinterview Communication dated Apr. 17, 2015 in U.S. Appl. No. 13/964,415, 5 pages.
First Action Interview Preinterview Communication dated Jun. 5, 2015 in U.S. Appl. No. 13/964,408, 6 pages.
First Action Interview Office Action dated Jun. 29, 2015 in U.S. Appl. No. 13/964,415, 7 pages.

* cited by examiner

MULTI-DISCIPLINARY TEAM WORKSPACE

CROSS-REFERENCE TO RELATED APPLICATIONS

This application, U.S. patent application Ser. No. 13/964,413, claims the benefit of priority to U.S. Provisional Application No. 61/842,125, filed Jul. 2, 2013, and entitled "Dynamic Association and Documentation and Multi-Disciplinary Team Workspace and Clinical Document Speed Viewer." The entirety of the aforementioned application is incorporated by reference herein.

This application, is also related by subject matter to U.S. patent application Ser. No. 13/964,408, entitled "Dynamic Association and Documentation"; and to U.S. patent application Ser. No. 13/964,415, entitled "Clinical Document Speed Viewer" and now abandoned, both of which are assigned or under obligation of assignment to the same entity as this application and both of which are expressly incorporated by reference herein. All three applications are being filed on the same date.

BACKGROUND

Although clinician workflow applications are numerous, they often address discrete tasks and require a clinician to access multiple different applications in order to fully address a clinical finding. For example, a clinician may discover that a patient has an abnormal potassium level when viewing, for example, a list of recent labs in a clinician workflow application. In order for the clinician to address the low potassium, the clinician may have to navigate away from the clinician workflow application and open an ordering application to associate the low potassium with an existing clinical order or to order potassium replacement therapy. Additionally, the clinician may have to open a clinical note application in order to associate the low potassium with an existing clinical note or to create a new clinical note addressing the low potassium. Having to navigate to multiple different workflows in order to fully address a problem results in inefficiency and increases the chances for error.

Another problem in today's highly-specialized healthcare world is the coordination of care for patients that have multiple medical problems. Such patients are often cared for by a multi-disciplinary care team made up of clinicians having different areas of expertise. For example, a patient having both gastro-intestinal problems and cardiovascular problems may be cared for by clinicians specializing in internal medicine, cardiology, and gastro-enterology. Coordinating care by these different specialists is challenging. In most cases, the specialists do not have access to workflows that detail the care given by each specialist. The result is again inefficiency, the possibility of redundant care, and increased chance of error.

Yet another problem faced by clinicians is the monumental task of searching through the voluminous quantity of clinical documents often associated with today's patients. An individual patient may have hundreds of clinical documents generated by everyone involved in the patient's care from dieticians to neurosurgeons. Traditional approaches to searching include presenting clinical documents in reverse chronological order and searching through the documents one-by-one.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, systems, methods, and computer-storage media for presenting a graphical user interface (GUI) that is used to facilitate the care of a patient by a multi-disciplinary care team. The GUI presents a list of declared clinical problems associated with the patient. For each clinical problem, one or more care team icons are presented; each icon identifies a care team that is addressing the clinical problem. Interaction with a care team icon initiates the presentation of information including the identity of the clinician on the care team responsible for the patient, any new orders or documents created by the clinician with respect to the clinical problem, contact information for the clinician, and information on when the clinician last rounded on the patient.

BRIEF DESCRIPTION OF THE DRAWINGS

Embodiments are described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-storage media for presenting a graphical user interface (GUI) that is used to facilitate the care of a patient by a multi-disciplinary care team. The GUI presents a list of declared clinical problems associated with the patient. For each clinical problem, one or more care team icons are presented; each icon identifies a care team that is addressing the clinical problem. Interaction with a care team icon initiates the presentation of information including the identity of the clinician on the care team responsible for the patient, any new orders or documents created by the clinician with respect to the clinical problem, contact information for the clinician, and information on when the clinician last rounded on the patient.

Figure 1:
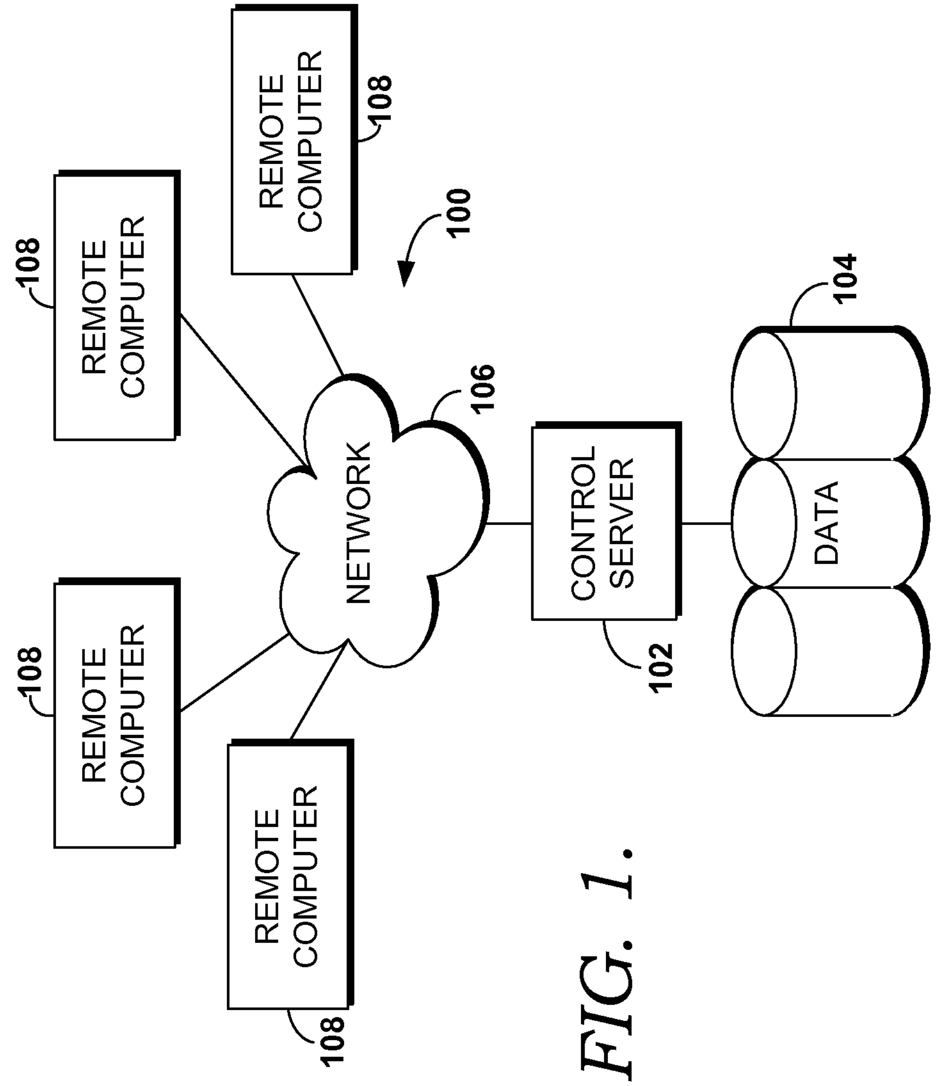
FIG. 1 is a block diagram of an exemplary computing environment suitable to implement embodiments of the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise non-transitory computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
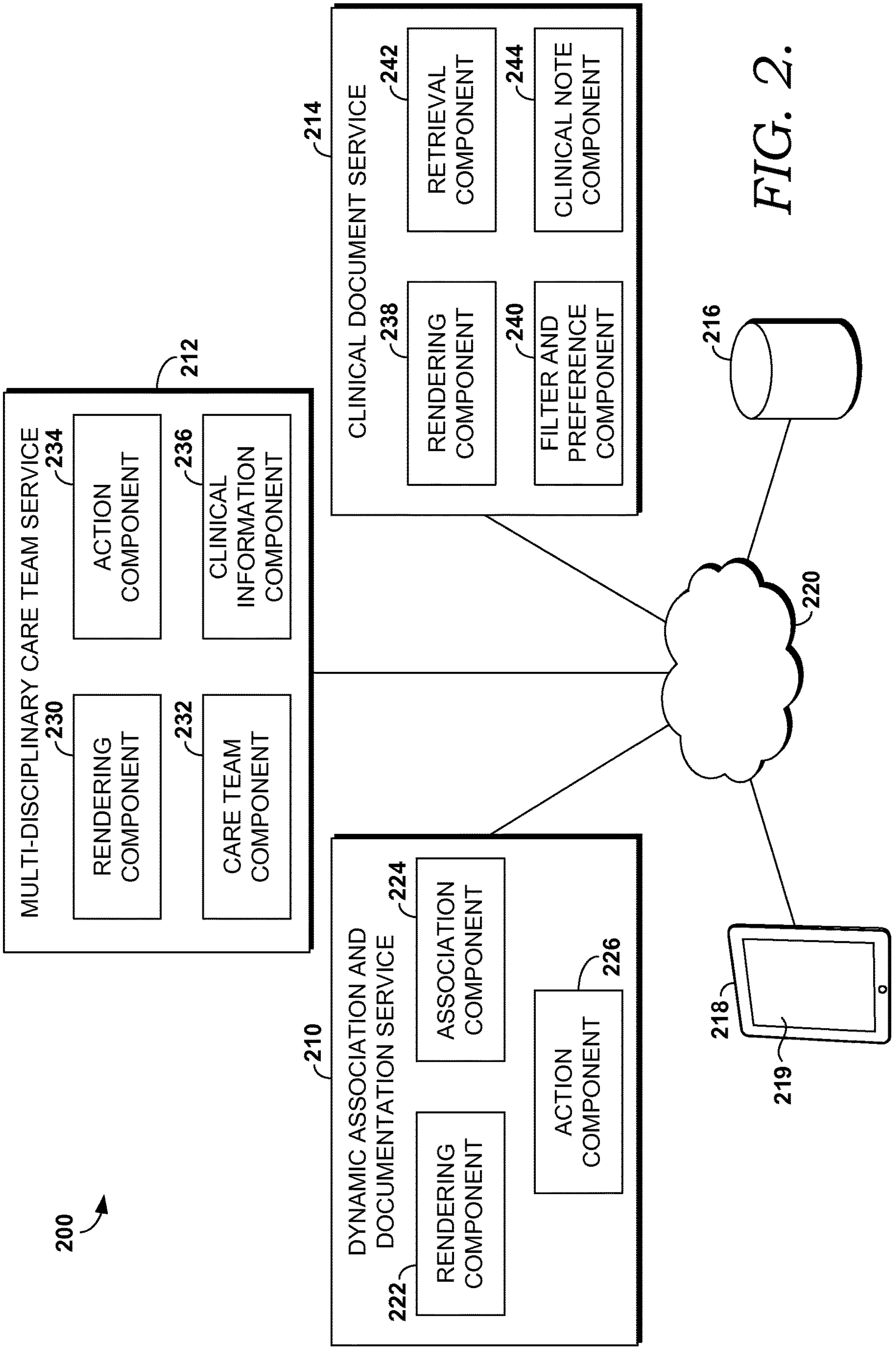
FIG. 2 is a block diagram of an exemplary system for generating graphical user interfaces useable for dynamically creating associations and taking actions with respect to an item of clinical information, facilitating care of a patient by a multi-disciplinary care team, and for searching clinical documents associated with the patient suitable to implement embodiments of the present invention.

Turning now to FIG. 2, an exemplary computing system environment 200 is depicted suitable for use in implementing embodiments of the present invention. The computing system environment 200 is merely an example of one suitable computing system environment and is not intended to suggest any limitation as to the scope of use or functionality of embodiments of the present invention. Neither should the computing system environment 200 be interpreted as having any dependency or requirement related to any single module/component or combination of modules/components illustrated therein.

The computing system environment 200 includes a number of services such as a dynamic association and documentation service 210, a multi-disciplinary care team service 212, and a clinical document service 214. Each of the services 210, 212, and 214 may be in communication with one another via a network 220. The network 220 may include, without limitation, one or more local area networks (LANs) or wide area networks (WANs). The network 220 may be a secure network associated with a healthcare facility. The secure network 220 may require that a user log in and be authenticated in order to send and/or receive information over the network 220. Additionally, each of the services 210, 212, and 214 are in communication with a data store 216 and an end-user computing device 218 having a display screen 219.

Although the services 210, 212, and 214 are depicted as separate services, it is contemplated that the services may be combined into one service. Additionally, although each service 210, 212, and 214 is depicted as having its own components, in reality a component, such as a rendering component may be shared by the different services 210, 212, and 214. The services 210, 212, and 214 are depicted separately to facilitate ease of explanation for each of the services 210, 212, and 214.

In some embodiments, one or more of the illustrated components/modules may be implemented as stand-along applications. In other embodiments, one or more of the illustrated components/modules may be integrated directly into the operating system of the services 210, 212, and 214. The components/modules illustrated in FIG. 2 are exemplary in nature and in number and should not be construed as limiting. Any number of components/modules may be employed to achieve the desired functionality within the scope of embodiments hereof. Further, the services 210, 212, and 214 may be located on any number of servers. By way of example only, the dynamic association and documentation service 210 might reside on a server, a cluster of servers, or a computing device remote from one or more of the remaining services.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The data store 216 is configured to store information for use by, for example, the services 210, 212, and 214 and the end-user computing device 218. The information stored in association with the data store 216 is configured to be searchable for one or more items of information stored in association therewith. The information stored in association with the data store 216 may comprise general information used by the services 210, 212, and 214 and/or the end-user computing device 218.

In one aspect, the data store 216 stores electronic medical records (EMRs) of patients associated with a healthcare facility. EMRs may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information.

Additionally, the data store 216 may store information concerning decision-support algorithms, differential or possible diagnoses algorithms, reference materials, standards of care, recommendation protocols, alert protocols, and the like. This information may be specific to a healthcare facility, or the information may be promulgated by, for example, nationally-recognized medical organizations or governing bodies. The data store 216 may also store information concerning staffing assignments and/or clinicians and care teams assigned to care for a patient as well as general information concerning the clinicians (e.g., office hours, office location, contact information, and the like).

The content and volume of such information in the data store 216 are not intended to limit the scope of embodiments of the present invention in any way. Further, though illustrated as a single, independent component, the data store 216 may, in fact, be a plurality of storage devices, for instance, a database cluster, portions of which may reside on the services 210, 212, and 214, the end-user computing device 218, and/or any combination thereof.

As shown, the end-user computing device 218 includes the display screen 219. The display screen 219 is configured to display information to the user of the end-user computing device 218, for instance, information relevant to communications initiated by and/or received by the end-user computing device 218, graphical user interfaces for dynamically creating associations and taking actions with respect to an item of clinical information, graphical user interfaces for facilitating patient care by a multi-disciplinary care team, graphical user interfaces for searching clinical documents, and/or the like. Embodiments are not intended to be limited to visual display but rather may also include audio presentation, combined audio/visual presentation, and the like. The end-user computing device 218 may be any type of display device suitable for presenting a graphical user interface. Such computing devices may include, without limitation, a computer, such as, for example, any of the remote computers 108 described above with reference to FIG. 1. Other types of display devices may include tablet PCs, PDAs, mobile phones, smart phones, as well as conventional display devices such as televisions. Interaction with the display screen 219 of the end-user computing device 218 may be through conventional methods such as a mouse or a touch pad; interaction with the display screen 219 may also occur through the use of gestures such as tapping, swiping, flicking, pinching, and the like.

The computing system environment 200 is merely exemplary. While the services 210, 212, and 214 are illustrated as single units, it will be appreciated that the services 210, 212, and 214 are scalable. For example, each service may in actuality include a plurality of computing devices in communication with one another. Moreover, the data store 216, or portions thereof, may be included within, for instance, the services 210, 212, and 214 as a computer-storage medium. The single unit depictions are meant for clarity, not to limit the scope of embodiments in any form.

Dynamic Association and Documentation

The dynamic association and documentation service 210 facilitates the presentation of a GUI that enables clinicians to address a clinical finding at the point it is encountered in a workflow. A clinical finding may encompass an item of clinical information such as a lab result, a procedure result, a clinical note, a clinical report, a radiograph, an EKG, an EEG, and the like. The GUI allows the clinician to associate the clinical finding with existing patient diagnoses and/or possible diagnoses related to the clinical finding. As well, the GUI enables the clinician to review historical information related to the finding and take actions with respect to the clinical finding. All this is accomplished without requiring the user to navigate away from the current workflow. Instead, the clinical finding is selected on the current workflow, and the GUI is presented as an overlay on the existing content of the workflow.

As shown in FIG. 2, the dynamic association and documentation service 210 comprises a rendering component 222, an association component 224, and an action component 226. In some embodiments, one or more of the components 222, 224, and 226 may be implemented as stand-alone applications. In other embodiments, one or more of the components 222, 224, and 226 may be integrated directly into the operating system of a computing device such as the remote computer 108 of FIG. 1. It will be understood that the components 222, 224, and 226 illustrated in FIG. 2 are exemplary in nature and in number and should not be construed as limiting. Any number of components may be employed to achieve the desired functionality within the scope of embodiments hereof.

The rendering component 222 of the dynamic association and documentation service 210 is configured to render a GUI upon a user selecting a clinical finding in a clinical workflow application. The GUI is presented such that it overlays existing content associated with the clinical workflow application. As used throughout this application, the term "clinical workflow application" or its equivalents encompasses a variety of clinical workflow applications. Such applications are numerous but may include an ordering workflow, a documentation workflow, a patient review workflow, a patient list workflow, and the like.

The rendering component 222 is configured to use the data stored in association with the data store 216 (e.g., electronic medical record information, reference materials, differential or possible diagnoses algorithms, and the like) to present information on the GUI. The information rendered by the rendering component 222 may include trending information related to the selected clinical finding. The trending information includes a historic overview of values or other attributes associated with the clinical finding and may be presented in association with a timeline. The timeline may further include one or more icons representing clinical documents and/or orders that reference or relate to the selected clinical finding. The icons, which are actionable, overlay the timeline at points in time corresponding to when the clinical document and/or order was created. A user can interact with an icon by selecting the icon, hovering over the icon, or executing a gesture with respect to the icon (e.g., tapping, swiping, etc.) to initiate a presentation of the clinical document and/or order associated with the icon. The information rendered by the rendering component 222 may also include labs and/or medications that are related to the clinical finding. The labs and/or medications may be deemed to be related based on explicit clinician linkages, reference materials, or based on an analysis of the statistical occurrence of the labs and medications with the selected item of clinical information.

The information presented by the rendering component 222 may also include a current problem list for the patient. The current problem list includes one or more problems that have previously been declared to be associated with the patient either automatically, and without human intervention, based on one or more rules or based on a clinician making the association. The rendering component 222 may also present one or more possible diagnoses related to the clinical finding. The possible diagnoses may be generated based on differential diagnoses algorithms stored in association with the data store 216. For example, a clinical finding of low potassium may be associated with possible diagnoses such as hypokalemia, hyperaldosteronism, diuretics, laxative abuse, and diarrhea. Each of the current problems and the possible diagnoses is selectable by a user. Selection causes the clinical finding to be electronically associated with the selected current problem and/or possible diagnosis in the patient's electronic medical record. This will be explored in greater depth below with respect to the association component 224.

Continuing, the rendering component 222 is further configured to present an action display area that includes one or more selectable actions that enable a user to initiate actions with respect to the clinical finding. The actions may include placing an order with respect to the clinical finding, associating the clinical finding with one or more documents such as a clinical note, communicating a message to another caregiver, the patient, or a member of the patient's family regarding the clinical finding, and/or reviewing a synopsis of the patient's medical history or a history of the clinical finding such as previous actions, documentation, comments, or orders taken with respect to the selected clinical finding.

The association component 224 of the dynamic association and documentation service 210 is configured to associate the selected clinical finding with one or more of a current declared patient problem, a possible diagnosis related to the clinical finding, and/or a new or existing clinical document. The declared association is stored in association with the patient's electronic medical record where it can be accessed by other clinician workflow applications. The association may be triggered in response to a user selecting a current problem or a possible diagnosis on the GUI, or by selecting an action that enables the user to associate the item of clinical information with, for example, a document such as a clinical note, a radiology report, a procedure report, and the like.

The action component 226 of the dynamic association and documentation service 210 is configured to present information associated with one or more actions and to initiate one or more actions selected by a user. As mentioned above, the rendering component 222 is configured to render an action display area with one or more selectable actions. Upon a user selection of an action, the action component 226 is configured to present information associated with the selected action. For instance, user selection of an ordering action initiates the display of, for example, an order profile for the patient, treatment guidelines for any current problems or possible diagnoses selected by the user, and suggested orders and/or order sets related to the current problems and/or possible diagnoses selected by the user. If the user selects a suggested order, the action component 226 is configured to initiate the order and store the order in association with the patient's electronic medical record.

Figure 6:
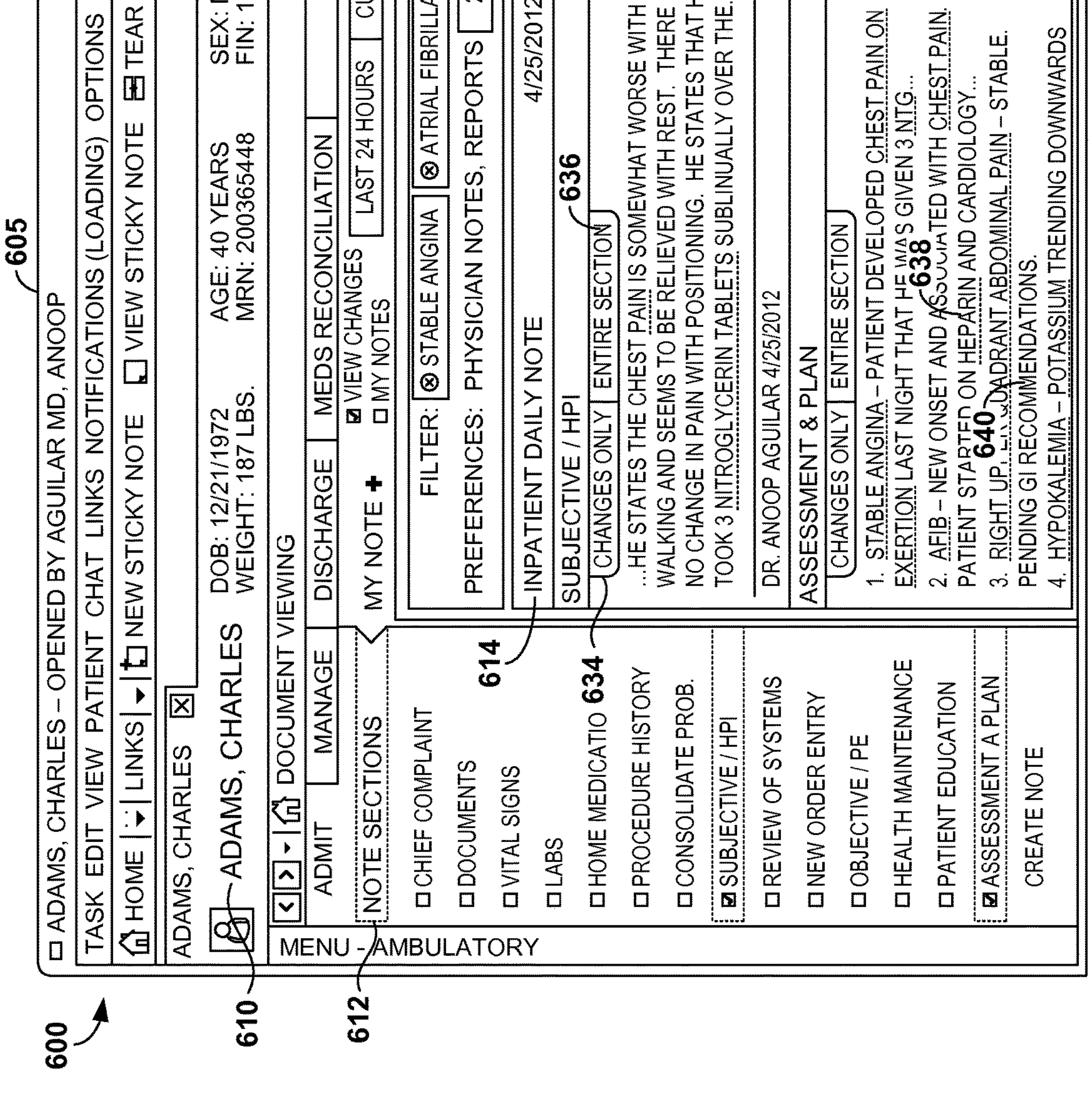
FIG. 6 is an exemplary graphical user interface useable for searching clinical documents associated with a patient in accordance with an embodiment of the present invention.
Figure 6A:
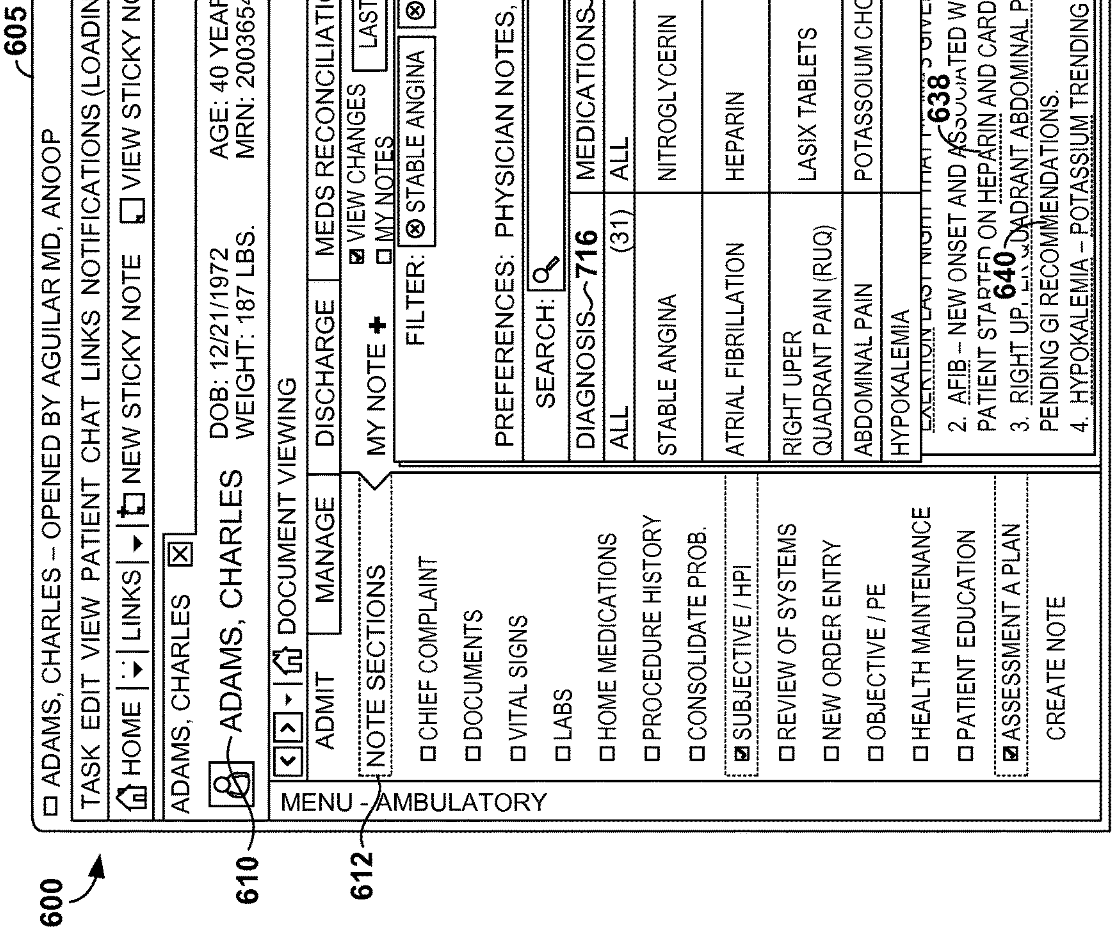
FIG. 6A depicts the exemplary graphical user interface of FIG. 6 and includes a filter selection area useable for selecting one or more clinical document filters in accordance with an embodiment of the present invention.

Selection of a document action causes the action component 226 to present, for example, a clinical document GUI similar to that shown in FIGS. 6 and 6A that enables the user to search for an existing clinical document and electronically associate the selected clinical finding with the existing clinical document. In addition to, or in the alternative, the clinician can create a new clinical document using the clinical document GUI and associate the clinical finding with the new clinical document. Additionally, the clinical document GUI also presents one or more clinically-relevant documentation aids based on the associated clinical finding or based on previous documented actions. The clinical document GUI will be explained in greater depth below.

Selection of a message action causes the action component 226 to present messaging options (e.g., instant messaging, e-mail, calling, and/or paging options), including the use of predefined messaging templates, and to facilitate the communication of any created messages. Selection of a history action causes the action component 226 to present a synopsis of the patient's medical history, previous clinical actions, comments, documentation, messages, and/or a review of the selected clinical finding.

Figure 3:
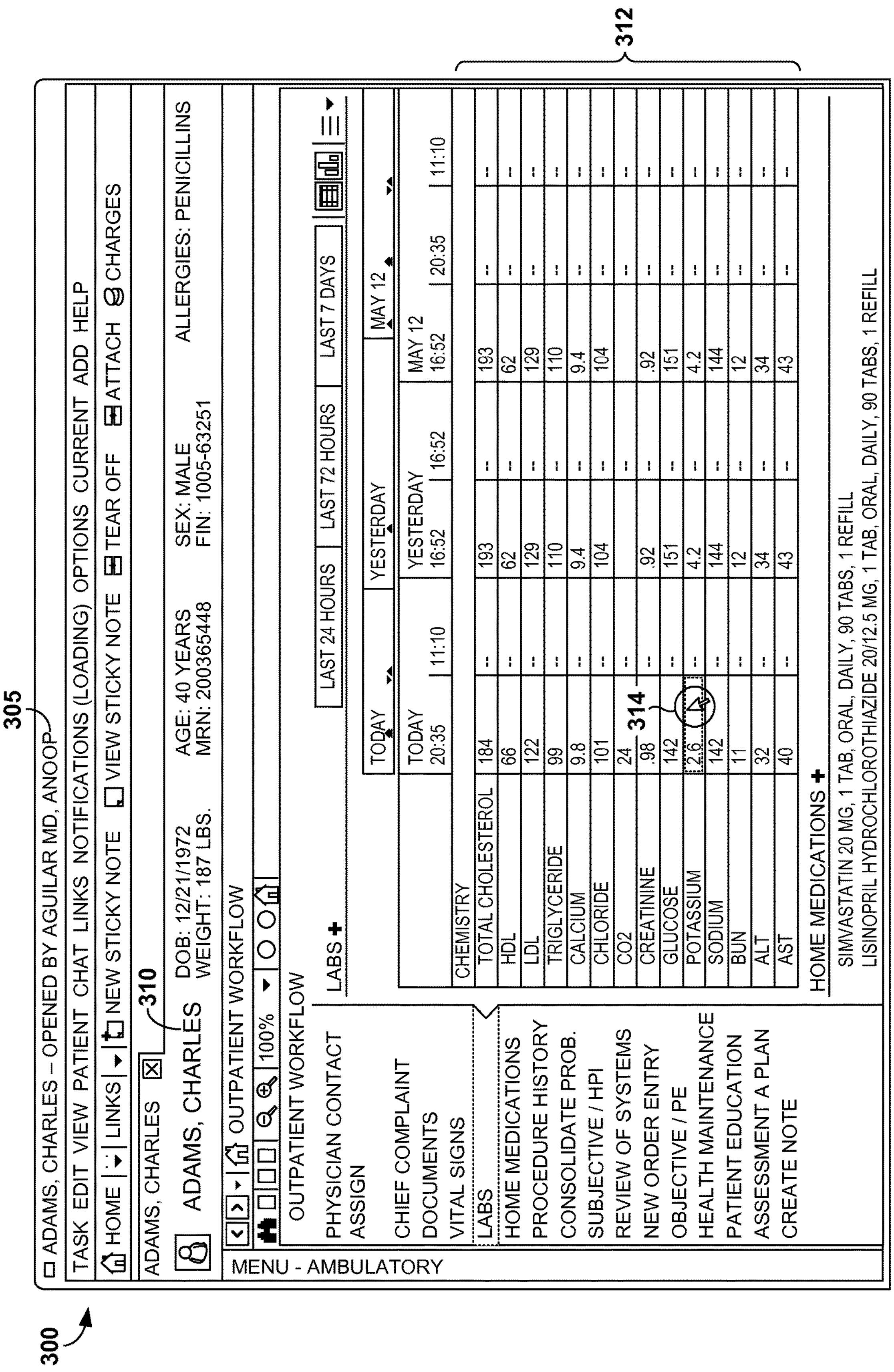
FIG. 3 is an exemplary graphical user interface demonstrating a clinician workflow in accordance with an embodiment of the present invention.

Turning to FIG. 3, FIG. 3 depicts an exemplary GUI 300 that is currently utilized by clinicians in their practice. The GUI 300 is an example of a clinical workflow application in which a clinician can review various types of information associated with a patient. In this case, a clinician 305 who is accessing the GUI 300 is identified (also known as the viewer 305), and a patient 310 who is the subject of the GUI 300 is also identified. Currently, the viewer 305 is reviewing labs 312 associated with the patient. The viewer 305 notices that the potassium value has been flagged as elevated, and, as shown by the numeral 314, the viewer 305 selects the abnormal potassium value. Although a lab value is shown as selected by the viewer 305, it is contemplated that the viewer 305 can select other clinical findings such as a medication, a report, clinical or health concepts within a clinical document, a device reading, a vital sign, and the like. Any and all such aspects, and any combination thereof, are contemplated as being within the scope of the invention.

Figure 4:
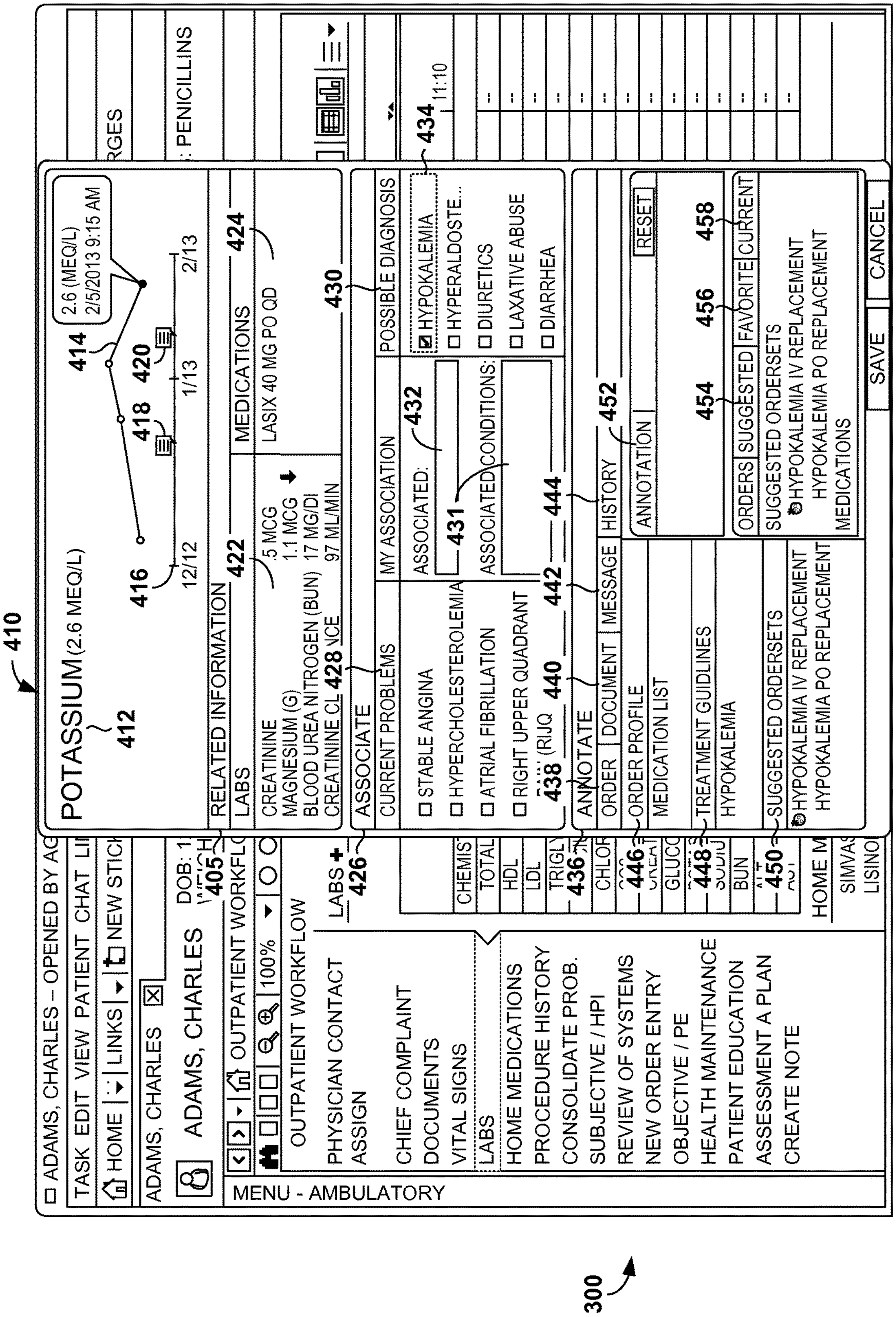
FIG. 4 is an exemplary graphical user interface for dynamically creating associations and taking actions with respect to an item of clinical information in accordance with an embodiment of the present invention.

FIG. 4 depicts an exemplary GUI 410 that is initiated upon the viewer 305 selecting, for example, the abnormal potassium value on the GUI 300 (the abnormal potassium value is now known as the clinical finding 412). The GUI 410 may also be initiated upon the viewer 305 selecting a medication, a clinical document, a health concept, a device reading, a vital sign, and the like. Although the GUI 410 is shown as being initiated upon selection of a lab value on the GUI 300, it is contemplated that the GUI 410 may be initiated from any clinician workflow application.

As seen, the GUI 410 overlays a portion of the content associated with the GUI 300. The GUI 410 includes several different display areas—a related information display area 405, an association display area 426, and an action display area 436. The related information display area 405 includes identifying information associated with the selected clinical finding 412 (e.g., a name and any current values associated with the clinical finding 412). The related information display area 405 also includes trending information 414 for the clinical finding 412. The trending information 414 may be presented in a graphical form with indications of when the clinical finding 412 was tested and any values associated with the tests; a user can hover over the indications and be presented with this information.

The related information display area 405 may also include an interactive timeline 416 having bounds corresponding to when the clinical finding 412 was first tested, created, ordered, measured, etc. and a current time. Actionable icons, such as icons 418 and 420, may overlay the timeline 416 and represent orders and/or documents that reference or relate to the clinical finding 412. The icons 418 and 420 overlay the timeline 416 at points in time corresponding to when the order and/or document was created. For example, the icon 418 may represent a set of orders that relate to or reference the clinical finding 412; it overlays the timeline 416 at a point in time corresponding to when the set of orders was created. Likewise, the icon 420 represents a clinical document that relates to and/or references the clinical finding 412; it also overlays the timeline 416 at a point in time corresponding to when the clinic document was created. Interaction with the icons 418 and/or 420 initiates a summary view of the orders and/or documents represented by the icons 418 and/or 420.

The related information display area 405 further includes a related labs area 422 that includes one or more lab values that have been determined to be related to the clinical finding 412. Additionally, a related medications area 424 is also shown that includes one or more medications that have been determined to be related to the clinical finding 412. The determination that the lab values and/or medications are related to the clinical finding 412 may be made based upon reference materials, explicit clinician linkages, and/or a statistical analysis of the co-occurrence of the clinical finding 412 with the lab value and/or medication.

The association display area 426 presents a list of one or more selectable current problems 428 associated with the patient, a list of one or more selectable possible diagnoses 430 related to the clinical finding 412, a search area 432, and an input area 431. The current problems 428 include those problems that have been previously identified to be associated with the patient. The possible diagnoses 430 relate to the clinical finding 412 and may be generated using differential diagnoses algorithms and/or reference materials stored in association with a data store such as the data store 216 of FIG. 2. When the clinical finding 412 is, for example, an abnormal lab value, the possible diagnoses 430 may include one or more medical conditions that may cause or be associated with the abnormal lab value. When the clinical finding 412 is, for example, a medication, the possible diagnoses may include medical conditions for which the medication is commonly taken and/or conditions caused by taking the medication. If the clinical finding 412 is, for example, a report or clinical document that references a medical condition, the possible diagnoses 430 may include additional medical conditions commonly associated with the referenced medical condition. The search area 432 enables a user to search for additional diagnoses not already associated with the patient or presented to the viewer. If an additional diagnosis is discovered using the search area 432, the additional diagnosis can be associated with the clinical finding 412. The input area 431 shows the list of associated diagnoses and enables the user to input any comments related to a created association.

As mentioned, each of the current problems 428 and each of the possible diagnoses 430 are selectable. Selection of one or more of these items, such as hypokalemia 434, creates an association in the patient's EMR between the selected item and the clinical finding 412. Thus, in the case of hypokalemia, an association in the patient's EMR would be made between the low potassium and the diagnosis of hypokalemia. Created associations are subsequently available to workflow applications accessing the patient's EMR. This feature obviates the need for a user to separately open each workflow application and document the association.

The action display area 436 includes a number of action tabs—an order action tab 438, a document action tab 440, a message action tab 442, and a history action tab 444—that enable a user to take action with respect to the clinical finding 412. Selection of one of the action tabs 438, 440, 442, or 444 initiates the presentation of information associated with the respective action. For example, as shown, selection of the order tab 438 initiates the presentation of an order profile 446 detailing any current orders associated with the patient, treatment guidelines 448 related to the selected current problem 428, possible diagnosis 430, or the clinical finding 412, and suggested order sets 450 for treatment of the selected current problem 428, possible diagnosis 430, or the clinical finding 412.

Additional information presented upon selection of the order tab 438 includes an annotation area 452 where the clinician can input annotations related to any new orders, as well as options for selecting suggested orders 454, favorite orders 456, and current orders 458. The suggested orders 454 can relate to the selected current problem 428 or possible diagnosis 430 and can include suggested order sets. Favorite orders 456 are customized based on the clinician who is accessing the GUI 410, and current orders 458 detail all current orders associated with the patient.

Selection of the document action tab 440 enables the user to associate a selected current problem 428 or possible diagnosis 430, and/or the clinical finding 412 with one or more of an existing clinical document such as a clinical note or a report, or with a new clinical document. Furthermore, selection of the document action tab 440 presents suggested clinical document templates, questionnaires, and/or other documentation aids. In one aspect, selection of the document tab 440 initiates the presentation of a GUI similar to that shown in FIG. 6. The GUI of FIG. 6 enables a clinician to quickly search through existing documents or create a new clinical document; this will be explained in greater depth below.

Selection of the message tab 442 initiates the presentation of one or more message options including instant message options, calling options, paging options, and e-mail options. The message options may include one or more predefined e-mail templates. Selection of the history tab 444 initiates the presentation of one or more of a synopsis of the patient's medical history, previous associated actions, and/or an overview of the information presented in the related information display area 405.

As seen, the dynamic association and documentation service 210 and its associated GUI 410 enable a clinician to address a clinical finding at the time it is discovered. The clinician can view clinical information related to the clinical finding, associate the clinical finding with a current problem, a clinical document, or a possible diagnosis, and/or take one or more actions related to the clinical finding. The clinician can fully address the clinical finding without having to navigate to multiple separate workflow applications.

Multi-Disciplinary Team Workspace

The multi-disciplinary care team service 212 facilitates the generation of a GUI that enables different care teams caring for a patient to, among other things, review actions taken by each of the care teams, review clinical information related to a patient problem, and initiate one or more actions with respect to a patient problem.

The multi-disciplinary care team service 212 comprises a rendering component 230, a care team component 232, an action component 234, and a clinical information component 236. In some embodiments, one or more of the components 230, 232, 234, and 236 may be implemented as stand-alone applications. In other embodiments, one or more of the components 230, 232, 234, and 236 may be integrated directly into the operating system of a computing device such as the remote computer 108 of FIG. 1. It will be understood that the components 230, 232, 234, and 236 illustrated in FIG. 2 are exemplary in nature and in number and should not be construed as limiting. Any number of components may be employed to achieve the desired functionality within the scope of embodiments hereof.

The rendering component 230 of the multi-disciplinary care team service 212 is configured to use the data stored in association with the data store 216 (e.g., electronic medical record information, reference materials, alerting protocols, differential diagnoses algorithms, staffing information, clinician assignments, etc.) to present information on a multi-disciplinary care team workspace GUI. The information presented by the rendering component 230 is customized based on the identity of the user accessing the GUI. The rendered information includes one or more declared clinical problems associated with a patient. The declared clinical problems may include possible diagnoses that were associated with an item of clinical information using, for example, the GUI 410 of FIG. 4. For each identified clinical problem, the rendering component 230 is configured to present alert information comprising one or more items that need to be addressed by the user, recommendations for treating the identified clinical problem, action icons representing actions that can be taken with respect to the clinical problem, care team icons representing care teams responsible for treating the clinical problem, clinical information icons representing clinical information associated with the identified problem, and any annotations related to the identified clinical problem. The annotations may comprise annotations created using the GUI 410 of FIG. 4.

Selection of an action icon causes the action component 234 to present information associated with the icon and to initiate one or more actions. The actions that can be taken with respect to the clinical problem may include review actions where the user can review clinical documentation related to the clinical problem, order actions where the user can place an order with respect to the clinical problem, document actions where the user can create a clinical document addressing the clinical problem, and communication actions where the user can initiate one or more communications (e.g., instant messaging, paging, e-mail, and/or calling) with respect to the clinical problem.

Care team icons represent care teams responsible for treating a given clinical problem. An individual clinical problem may be associated with more than one care team. For example, a patient suffering from atrial fibrillation may be cared for by an internal medicine care team and a cardiovascular care team. Selection of a care team icon causes the care team component 232 to present information associated with the selected care team icon. This information may include the identity of a clinician on the care team who is assigned to care for the patient as well as office hours for that clinician. Additional information includes recent orders created by the clinician for the clinical problem, recent documents created by the clinician that address the clinical problem, information on when the clinician last rounded on the patient, and options for contacting the clinician including instant messaging options, e-mail options, paging options, and calling options.

Clinical information icons represent various types of clinical information associated with a clinical problem. Exemplary types of clinical information includes currently prescribed medications being used to treat the clinical problem, existing clinical documents that relate to or reference the clinical problem, laboratories related to the clinical problem, radiology images and/or reports related to the clinical problem, surgery reports associated with the clinical problem, and any messages that reference the clinical problem. Selection of one of the clinical information icons causes the clinical information component 236 to present the information associated with the icon.

The clinical information icons may be rendered by the rendering component 230 in a variety of states. For example, a clinical information icon may be presented in tagged state indicating that information associated with the icon has been tagged by another clinician for review by the viewer of the GUI. A review state indicates that clinical information associated with the icon has not been previously reviewed by the viewer of the GUI. A previously-viewed state indicates that the clinical information associated with the icon has been previously viewed by the viewer of the GUI, and a no-information state indicates that there is currently no clinical information associated with the icon.

The rendering component 230 is further configured to present one or more selectable identified clinical findings associated with the patient. The clinical findings are identified by accessing the patient's EMR and identifying pertinent clinical findings. Upon selection of one or more of the identified clinical findings, the rendering component 230 may utilize differential diagnoses algorithms stored in a data store, such as the data store 216 of FIG. 2, to present one or more selectable possible diagnoses related to the selected findings. Further, some of these possible diagnoses may be flagged as high risk. Additionally, upon selection of one of the possible diagnoses, a summary may be initiated that explains why the multi-disciplinary care team service 212 generated that particular diagnosis.

Figure 5:
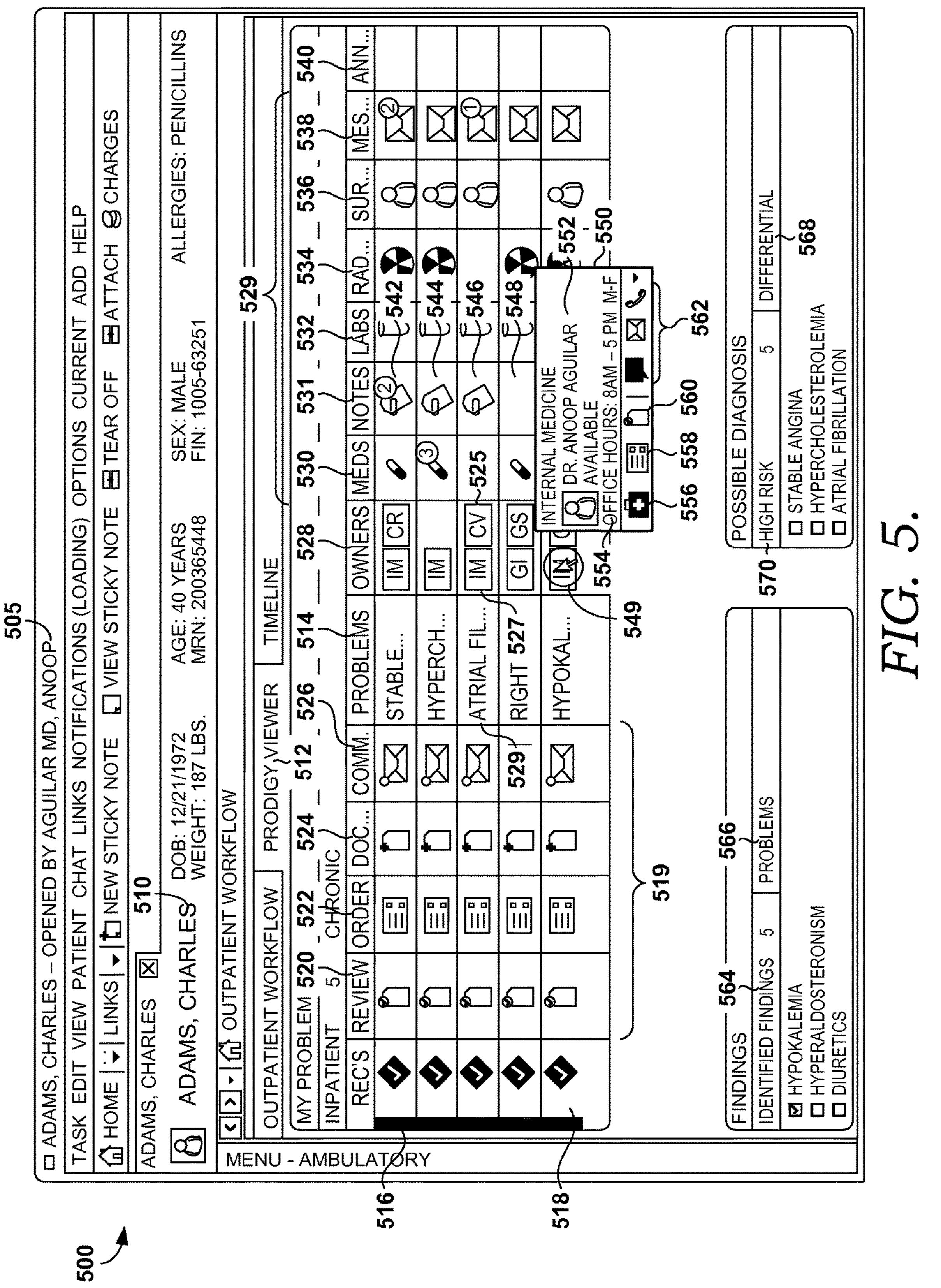
FIG. 5 is an exemplary graphical user interface useable for facilitating patient care by a multi-disciplinary care team in accordance with an embodiment of the present invention.

FIG. 5 depicts an exemplary GUI 500 generated by the multi-disciplinary care team service 212. The GUI 500 includes an area that identifies a clinician or viewer 505 accessing the GUI 500 and an area that identifies the patient 510. As mentioned above, the information presented on the GUI 500 is customized based on the identity of the viewer 505. The GUI 500 may be initiated upon the viewer 505 selecting a tab 512 (e.g., "Prodigy Viewer"). The GUI 500 includes a declared clinical problem display area 514 that displays one or more clinical problems associated with the patient. Some of these clinical problems may have been declared using the GUI 410 of FIG. 4. Each patient problem in the clinical problem display area 514 may be associated with alerts, recommendations, action icons, care team icons, clinical information icons, and annotations.

For example, alert display area 516 presents visual indicators used to alert the viewer 505 to one or more items that need to be addressed for a particular patient problem. The visual indicators may be shaded different colors to indicate the existence or absence of an alert related to one of the clinical problems in the clinical problem display area 514. A recommendation display area 518 presents indicators indicating whether recommendations exist for a particular patient problem. The user can select the indicator and be presented with a list of recommendations related to the clinical problem.

An action display area 519 includes one or more action icons such as review icons 520, order icons 522, document icons 524, and communication icons 526 related to a clinical problem. Selection of the review icon 520 for a clinical problem initiates the presentation of one or more clinical documents that reference or relate to the clinical problem. Alternatively, selection of the review icon 520 may initiate a summary of information related to the declared clinical problem. Selection of the order icon 522 for a clinical problem initiates an ordering screen where the user can create an order related to the patient problem. Selection of a document icon 524 for a clinical problem initiates a user interface where the user can create a clinical document such as a clinical note related to the clinical problem. In one aspect, the user interface initiated upon selection of the document icon 514 may be similar to the GUI shown in FIG. 6. Selection of a communication icon 526 for a clinical problem initiates one or more options (e.g., instant messaging, paging, e-mail, calling) for communicating with another caregiver on the patient's care team.

A care team display area 528 is configured to present one or more care team icons where each icon gives an indication of the care team(s) currently assigned to care for a particular patient problem. For instance, care team icons 525 and 527 indicate that an internal medicine care team and a cardiovascular care team have been assigned to care for the patient problem "Atrial Fibrillation" 529. Each of the care team icons in the care team display area 528 is actionable. Interaction with a care team icon such as care team icon 549 initiates the presentation of care team information 550. The care team information 550 includes an identity of a clinician 552 on the care team who is currently assigned to care for the patient. The care team information 550 also includes office hours 554 for the clinician 552. Additionally, the care team information 550 includes rounding icon 556, order icon 558, clinical document icon 560, and communication icons 562. Interaction with the rounding icon 556 provides information on when the clinician 552 last rounded on the patient. Interaction with the order icon 558 presents information on orders entered by the clinician 552 for the particular clinical problem, and interaction with the clinical document icon 560 presents information on clinical documents created by the clinician 552 for the patient problem. Selection of one of the communication icons 562 enables the viewer 505 to initiate one or more communication paths with the clinician 552.

Clinical information review icons 529 include actionable medication review icons 530, note review icons 531, lab review icons 532, radiology review icons 534, surgery review icons 536, and message review icons 538. Each of the icons 530, 531, 532, 534, 536, and 538 may be presented in one of several states. A tagged state is shown by note review icon 542 and indicates that information associated with the note review icon 542 has been tagged by another clinician for review by the viewer 505. Additionally, the tagged state may be created based on the information associated with the note review icon 542 meeting predefined criteria. For example, the information may comprise a lab value that is outside the normal range, and this may trigger the icon 542 to be presented in a tagged state. The tagged state may be shown as a solid outline of the icon 542 along with a number indicating the number of items that need to be reviewed. A review state is shown by note review icon 544 and indicates that clinical information associated with the note review icon 544 has not been previously reviewed by the viewer 505. A review state may be shown as a solid outline of the icon 544. A previously-viewed state is shown by note review icon 546 and indicates that clinical information associated with the note review icon 546 has been previously viewed by the viewer 505. A previously-viewed state may be shown by graying out the outline of the icon 546. A no-information state is shown by an absence of an icon (as shown by numeral 548) and indicates that there is no clinical information available. Other ways of indicating an icon state are contemplated as being within the scope of the invention and include such ways as color-coding, altering the shape of the icon, and the like.

The medication review icons 530 provide information concerning medications that are currently prescribed for a particular clinical problem, and note review icons 531 provide information concerning clinical documents that relate to and/or reference the particular patient problem. The lab review icons 532 present information about laboratory values/readings related to the particular patient problem, and the radiology review icons 534 present radiology reports and/or images related to the patient problem. The surgery review icons 536 present information such as procedure or surgery reports that are related to the particular patient problem, and the message review icons 538 present messages from, for example, other members of the patient's care teams that relate to the particular patient problem.

The GUI 500 further comprises an annotation display area 540 that presents any annotations that have been documented for a particular clinical problem including those annotations documented using the GUI 410 of FIG. 4. An identified findings display area 564 presents selectable clinical findings that have been identified for the patient. The clinical findings may have been identified by accessing the patient's EMR and analyzing the information contained therein to identify clinical findings of significance. The viewer 505 of the GUI 500 can select one or more of the findings and be presented with possible diagnoses 568 that relate to the selected finding(s). Further, at least a portion of the possible diagnoses 568 may be flagged as high risk 570 to further draw the viewer's attention to possible problems. The generation of the possible diagnoses 568 and the high risk diagnoses 570 may be based on differential diagnoses algorithms stored in association with a data store such as the data store 216 of FIG. 2. The viewer 505 can select one of the possible diagnoses 568 to initiate a summary that explains why the possible diagnosis 568 was selected in relation to the selected identified findings 564.

By way of illustrative example, a patient's EMR may be accessed and clinical findings of night sweats and atypical pneumonia may be identified. The clinical findings are presented in the identified findings display area 564. The viewer 505 can select both of these clinical findings and be presented with possible diagnoses 568 of AIDS and lymphoma. Further, the diagnosis of AIDS may be flagged as high risk to draw the viewer's attention. The viewer 505 can select the AIDS diagnosis and be presented with information on how the AIDS diagnosis relates to the selected clinical findings.

The multi-disciplinary care team service 212 and its associated GUI 500 assist care teams in their management of patients with multiple medical problems. A member of the care team can access the GUI 500 and quickly review each care team's contributions to the patient's care as well as patient clinical information. Additionally, the GUI 500 enables the care team member to take actions with respect to a particular patient problem and to review identified clinical findings for the patient.

Clinical Document Speed Viewer

The clinical document service 214 of FIG. 2 is configured to generate a GUI that enables a clinician to quickly search through all the clinical documents, such as daily notes and/or reports, associated with a patient. Preferences can be set that define which types of clinical documents to be considered, thus allowing a clinician to exclude clinical documents that may not be relevant to the current review process. For example, an ambulatory doctor may choose to exclude inpatient nurse assessment notes. Additionally, the clinician can set preferences specifying authors of clinical documents to be searched. The clinician can further filter the documents based on criteria such as health concepts that have been identified for the patient. Selected documents that meet filter and preference criteria can be quickly searched by restricting the document to specified document sections and only presenting information that has not previously been reviewed by the user of the GUI.

The clinical document service 214 comprises a rendering component 238, a filter and preference component 240, a retrieval component 242, and a clinical document component 244. In some embodiments, one or more of the components 238, 240, 242, and 244 may be implemented as stand-alone applications. In other embodiments, one or more of the components 238, 240, 242, and 244 may be integrated directly into the operating system of a computing device such as the remote computer 108 of FIG. 1. It will be understood that the components 238, 240, 242, and 244 illustrated in FIG. 2 are exemplary in nature and in number and should not be construed as limiting. Any number of components may be employed to achieve the desired functionality within the scope of embodiments hereof.

The rendering component 238 of the clinical document service 214 is configured to use the data stored in association with the data store 216 (e.g., electronic medical record information) to present information on a clinical document workspace GUI. The information presented by the rendering component 238 includes a searchable timeline having bounds corresponding to when a clinical document was first documented for a patient to the current point in time. The searchable timeline includes a plurality of actionable icons representing clinical documents associated with the patient. The icons are overlaid on the timeline at points in time corresponding to when the icon's respective clinical document was created. The icons are variably shaded or colored to indicate the application of one or more filters and/or preferences. For instance, icons representing documents that meet user preferences may be shaded a dark grey or black, while icons representing documents that do not meet user preferences may be shaded a light grey. Further, icons representing documents that meet filter criteria may be shaded a color such as green. These examples of shading and colors are meant to be exemplary only, any way of shading or coloring the icons to indicate satisfaction of preference or filter criteria is contemplated as being within the scope of the invention. Further, the icons may be variably sized to indicate the number of clinical documents associated with a particular icon.

Interaction with an icon by, for example, hovering over the icon, may initiate the presentation of a date and time when the respective document was created. Alternatively, or in addition to, interaction with the icon may initiate a thumbnail view of the respective document. Selection of an icon on the searchable timeline by, for example, clicking on the icon or using a tapping or swiping gesture, causes the retrieval component 242 to retrieve the respective clinical document from the patient's EMR; the retrieved document is subsequently presented to the viewer of the GUI.

The rendering component 238 is further configured to present one or more selectable document section options on the GUI. Exemplary document section options may include chief complaint, documents, vital signs, labs, home medications, diagnostics, procedure history, consolidated problems, subjective or history of present illness, review of systems, new order entry, objective or physical exam, health maintenance, patient education or follow-up, and/or assessment and plan. A viewer of the GUI can select one or more document section options and restrict a displayed document to the selected section(s). The document sections may have been identified in the displayed document using natural language processing.

The rendering component 238 is additionally configured to present one or more preference options and one or more filter options to a viewer of the GUI. Selection of a preference and/or filter option causes the filter and preference component 240 to restrict the patient's clinical documents to those that meet the preference and filter criteria. As explained above, this may be shown visually by variably shading and/or coloring the icons representing the clinical documents on the searchable timeline. Preference options may include options to restrict clinical documents based on author or role type (e.g., clinical documents authored by a physician versus clinical documents authored by a physical therapist or patient), and/or options to restrict clinical documents based on the type of document (e.g., daily note versus radiology report). Further, preference options may include options to restrict clinical documents based on timeframe or numeric count (e.g., clinical documents generated in the last six month or the most-recent 100 clinical documents), and options to restrict based on encounter type or venue (e.g., clinical documents generated during ambulatory visits versus clinical documents generated during inpatient stays). Additional preference options include options to restrict clinical documents based on clinical service (e.g., hospitalist team versus surgical team) or provider type (e.g., specialist versus level of training such as a medical student or resident).

Filter options are based on health concepts associated with the patient. Health concepts associated with the patient may include declared diagnoses associated with the patient, medications associated with the patient, and tests and procedures associated with the patient. Health concepts may be associated with the patient based on a clinician making an explicit association between a clinical finding and a possible diagnosis using the GUI 410 depicted in FIG. 4.

The rendering component 238 may additionally present the health concepts associated with the patient as a separate side bar on the GUI. The health concepts may be categorized under category headings such as diagnosis, medications, tests, and procedures. A viewer of the GUI can select a health concept to access reports or other documentation that relate to or reference the selected health concept. Alternatively, or in addition to, the viewer can select a health concept and initiate the presentation of an association GUI as exemplified by the GUI 410 of FIG. 4. Utilizing this GUI, the viewer can associate the health concept with a declared diagnosis, a possible diagnosis, a clinical document, and the like as explained above in relation to the GUI 410 of FIG. 4.

Once a clinical document has been selected and presented on the GUI by the rendering component 238, the clinical document component 244 utilizes the health concepts associated with the patient to highlight key terms in the presented document. Highlighting may be through bolding the key terms or shading the key terms a different color than the rest of the document contents. The clinical document component 244 is further configured to grey out those portions of the presented document that have previously been viewed by the viewer of the GUI thereby enabling the viewer to target previously unviewed text. The highlighted key terms are selectable. Upon selection of a key term, a GUI similar to the GUI 410 of FIG. 4 is initiated enabling the viewer to associate the selected term with a declared patient problem, a possible diagnosis related to the selected key term, a clinical document, and the like.

Turning now to FIG. 6, FIG. 6 depicts an exemplary clinical document speed viewer 600 illustrating aspects discussed above. The GUI 600 includes an area identifying a viewer 605 of the GUI 600. Additionally, the GUI 600 includes an area identifying the patient 610. The GUI 600 includes several different display areas include a note section display area 612, a clinical document display area 614, a preference selection area 620, a filter selection area 622, a searchable timeline display area 616, and a health concepts display area 624. The note section display area 612 is configured to present one or more document section options. Selection of a document section option restricts any displayed clinical document to the selected section(s).

The clinical document display area 614 is configured to enable the viewer 605 to generate a new clinical document. As well, the clinical document display area 614 is configured to present an existing clinical document selected by the viewer 605. Those portions of the clinical document corresponding to selected note sections are presented. If the viewer 605 does not restrict the document to one or more specified note sections using the note section options presented in the note section display area 612, then the entire clinical document will be presented.

The clinical note display area 614 includes a "changes or differences only" option 634 and an "entire section" option

636. Selection of the "changes or differences only" option 634 restricts the presented information to content that has not previously been reviewed by the viewer 605. Content that has previously been viewed may be grayed out or hidden from view. This is true even if the content was reviewed by the viewer in another clinical document by the same author, in another clinical document by a different author, or in another section of the current clinical document. Selection of the entire section option 636 causes all of the content of the presented clinical document to be shown regardless of whether portions of the content have been previously viewed. As mentioned earlier, key terms in the presented document that are associated with identified patient health concepts may be highlighted—this is shown by the numerals 638 and 640. Highlighting may be through bolding, underlining, shading or coloring, and the like.

The searchable timeline 616 is presented as a vertical timeline adjacent to the clinical document display area 614. Although shown as a vertical timeline, it is contemplated that the searchable timeline 616 may be presented in different configurations such as a horizontal timeline. The searchable timeline 616 has a time span encompassing the lifetime record of the patient's clinical documents (e.g., 2011 to 2013 as shown in FIG. 6). The searchable timeline 616 includes a plurality of interactive icons representing clinical documents. Interaction with an icon, such as hovering over an icon, initiates the presentation of a date and time when the document was created. This is shown by the numeral 618. Hovering over an icon may additionally initiate the presentation of a thumbnail image of the document represented by the icon. Selection of an icon initiates the presentation of the clinical document associated with the icon in the clinical document display area 614.

The preference selection area 620 includes options for the viewer 605 to set one or more preferences as outlined above. Preferences may be based on author of the clinical document, type of document, timeframe, numeric count, encounter type, venue, clinical service, provider type, and the like. The filter selection area 622 presents filters that have previously been selected by the viewer 605. In this case, the viewer has selected to filter the clinical documents by two of the patient's diagnoses—stable angina and atrial fibrillation. Those documents that relate to or reference these diagnoses will be highlighted on the searchable timeline 616 by, for example, coloring the icons representing the desired documents differently from the other icons.

FIG. 6A depicts the presentation of filter options. As described above, the filter options correspond to health concepts that have been identified for the patient 610. FIG. 6A includes selected filters 710 which correspond to the selected filters 622 of FIG. 6. FIG. 6A further includes one or more additional filter options that are categorized by diagnosis 716, medications 718, tests 720, and procedures 722. Each of the filter options is selectable and can be selected to further filter the patient's clinical documents. FIG. 6A further includes a search box 714 by which the viewer 605 can search for health concepts associated with the patient.

Returning to FIG. 6, the GUI 600 further includes the health concepts display area 624. The health concepts display area 624 presents health concepts that have been identified for the patient 610 either based on the patient's electronic medical record or based on a currently displayed clinical document. The health concepts are categorized based on, for example, diagnosis 626, medications 628, tests 630, and procedures 632. Interaction with one of the health concepts in the health concepts display area 624 may initiate the presentation of clinical documents that relate to or reference the selected health concepts. Additionally, interaction with one of the health concepts may initiate a GUI similar to the GUI 410 of FIG. 4 that enables the viewer 605 to associate the selected health concept with one or more declared patient problems, possible diagnoses related to the selected health concept, a clinical document, and the like.

The clinical document service 214 and its associated GUI 600 enable a clinician to quickly search through a patient's clinical documents. The ability to filter clinical documents by identified health concepts, restrict displayed clinical documents by selected document sections, and view previously unviewed content and/or key terms within a selected document further speeds up the search process.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. One or more non-transitory computer-storage media having computer-useable instructions embodied thereon that, when executed by a computing device, cause the computing device to perform a method for facilitating the care of a patient by a multi-disciplinary care team, the method comprising:

determining, by the computing device, one or more declared clinical problems associated with the patient, wherein the one or more declared clinical problems comprise at least one of a complaint given by the patient, an undiagnosed symptom or a possible diagnosis previously associated with the patient;

displaying a declared clinical problem display area configured to display the one or more declared clinical problems;

determining, by the computing device, a first care team associated with the patient, the first care team comprising a set of multi-disciplinary specialists, each specialist assigned to at least one of the one or more declared clinical problems according to an expertise of the each specialist;

displaying, by the computing device, a care team display area configured to display for each of the one or more declared clinical problems associated with the patient one or more actionable care team icons;

receiving, by the computing device, a selection of at least one of the care team icons, the at least one of the care team icons corresponding to a first clinical problem of the one or more declared clinical problems;

specifically identifying, by the computing device, by interacting with a first care team icon, at least one specialist associated with the first care team upon receiving the selection;

providing, by the computing device, information relating to the at least one specialist by overlaying a care team information display on at least a portion of the declared clinical problem display area and a portion of the care team display area, wherein the care team information display a set of second care team icons including at least one of a rounding icon, order icon, clinical document icon, and one or more communication icons;

initiating, by the computing device, by interacting with the clinical document icon associated with the at least one specialist, a presentation of documentation created by the at least one specialist on the first care team for the first clinical problem; and determining and presenting a set of orders for the first clinical problem.

2. The method of claim 1, wherein interaction with the one or more care team icons further causes the computing device to initiate presentation of a further set of information comprising new orders initiated by the at least one specialist for the first clinical problem and rounding information related to the at least one specialist and the patient.

3. The method of claim 2, wherein the set of information further comprises one or more options for facilitating communication with the at least one specialist, wherein the one or more options comprise at least instant messaging, electronic mal, paging, or telephone.

4. One or more non-transitory computer-storage media having computer-useable instructions embodied thereon that, when executed by a computing device, cause the computing device to perform a method of proving a user interface for facilitating the care of a patient by a multi-disciplinary care team, the method comprising:

determining, by the computing device, an identity of a viewer of the user interface;

displaying, by the computing device, one or more declared clinical problems associated with the patient in a declared clinical problem display area, wherein the one or more declared clinical problems comprise at least one of a complaint given by the patient, an undiagnosed symptom, and a possible diagnosis previously associated with the patient, and wherein information presented on the declared clinical problem display area is automatically customized based on the determined identity of the viewer of the declared clinical problem display area;

for each declared clinical problem in the declared clinical problem display area, the method further comprising:

(1) visually indicating, by the computing device, in an alert display area, the existence of one or more items assigned to the viewer accessing the declared clinical problem display area, the one or more items displayed on a to-do list for the declared clinical problem, wherein the one or more items are customized based on a role within the multi-disciplinary care team of the viewer accessing the declared clinical problem display area;

(2) determining and presenting, by the computing device, one or more recommendations related to the declared clinical problem in a recommendation display area;

(3) determining and presenting, by the computing device, one or more actions with respect to the declared clinical problem and associating each of the one or more actions with a clinical action icon, wherein the one or more clinical action icons comprise at least one of:

a) an order action icon, interaction with which enables the viewer to initiate an order for the declared clinical problem, b) a document action icon, interaction with which enables the viewer to create a clinical document related to the declared clinical problem and associate the clinical document with a clinical finding and the viewer, or c) a communication action icon, interaction with which initiates the presentation of a message screen to facilitate communication with one or more clinicians;

(4) identifying, by the computing device, by interacting with a care team icon, one of more care teams associated with the declared clinical problem and associating each of the one or more care teams with one or more actionable care team icons in a care team display area; and enabling the viewer to interact with clinical information stored in a memory related to the declared clinical problem by using clinical information icons in a clinical information display area.

5. The method of claim 4, wherein for each declared clinical problem in the declared clinical problem display area, the method further comprises displaying an annotation display area configured to present annotations associated with the declared clinical problem.

6. The method of claim 4, wherein the one or more recommendations displayed in the recommendation display area are generated using clinical-support guidelines.

7. The method of claim 4, wherein the clinical document comprises a clinical note.

8. The method of claim 4, wherein interaction with the care team icon initiates the presentation of information stored in a memory comprising an identity of the clinician on the respective care team who is responsible for addressing the declared clinical problem.

9. The method of claim 8, wherein the information presented in response to the interaction with the care team icon further comprises new orders initiated by the clinician for the declared clinical problem, new clinical documentation created by the clinician for the declared clinical problem, and rounding information related to the clinician and the patient.

10. The method of claim 4, wherein the one or more clinical information display icons comprise at least one of:

a medication icon, interaction with which initiates presentation of information concerning prescribed medications for the declared clinical problem, a note icon, interaction with which initiates presentation of information concerning clinical documents referencing the declared clinical problem, a lab icon, interaction with which initiates presentation of information about laboratory values related to the declared clinical problem, a radiology icon, interaction with which initiates presentation of at least one of a radiology report and a radiology image related to the declared clinical problem, a surgery icon, interaction with which initiates presentation of at least one of a procedure report and a surgery report related to the declared clinical problem, or a message icon, interaction with which initiates presentation of messages from care team members.

11. The method of claim 10, wherein one or more states are determined for each of the one or more clinical information display icons and the one or more states are presented, the one or more states comprising:

a tagged state indicating that information associated with the clinical information display icon has been tagged by another clinician for review by the viewer of the declared clinical problem display area, a previously-viewed state indicating that information associated with the clinical information display icon has previously been reviewed by the viewer of the declared clinical problem display area, and a no-information state indicating that no information associated with the clinical information display icon has been documented.

12. The method of claim 4, wherein the one or more clinical findings are determined by accessing the patient's electronic medical record.

13. The method of claim 4, wherein at least a portion of the one or more possible diagnoses are flagged as high risk.

14. The method of claim 4, wherein interaction with at least one of the one or more possible diagnoses initiates a summary of information stored in memory concerning the reason the at least one possible diagnosis was presented.

15. One or more non-transitory computer-storage media having computer-useable instructions embodied thereon that, when executed by a computing device, performs a method of facilitating the care of a patient by a multi-disciplinary care team, the method comprising:

displaying, by the computing device, a declared clinical problem display area configured to present one or more declared clinical problems associated with the patient;

indicating an identity of a care team associated with a respective declared clinical problem by presenting, by the computing device, care team icons for each of the one or more declared clinical problems in a care team display area;

determining, by the computing device, at least one state relating to information associated with one or more clinical action icons, wherein a determination that the information has been tagged by another clinician is associated with a tagged state, wherein a determination that the information has been previously viewed by a current user is associated with a previously viewed state, and wherein a determination that there is no information associated with a clinical action icon is associated with a no-information state;

presenting, by the computing device, the one or more clinical action icons in accordance with the at least one determined state;

enabling the current user to initiate a clinical action with respect to at least one of the one or more declared clinical problem by interacting, by the computing device, with the one or more clinical action icons, wherein the one or more clinical action icons comprise at least one of an order icon for creating an order related to the declared clinical problem, a document icon for initiating a user interface for creation of a clinical document, and a communication icon for initiating one or more options for communicating with another care-giver on the patient's care team;

presenting, by the computing device, one or more clinical information display icons in a clinical information display area; and enabling the current user to view or interact with clinical information, stored in a memory, related to at least one of the one or more declared clinical problems by interacting, by the computing device, with the one or more clinical information display icons.

* * * * *

UNITED STATES PATENT AND TRADEMARK OFFICE
CERTIFICATE OF CORRECTION

PATENT NO. : 10,915,222 B2
APPLICATION NO. : 13/964413
DATED : February 9, 2021
INVENTOR(S) : Michael A. Ash et al.

Page 1 of 1

It is certified that error appears in the above-identified patent and that said Letters Patent is hereby corrected as shown below:

In the Claims

Column 21, Line 16: Please remove "mal" and replace with --mail--.

Column 21, Line 64: Please remove "one of more" and replace with --one or more--.

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*